United States Patent
Tanner et al.

(10) Patent No.: US 9,034,606 B2
(45) Date of Patent: May 19, 2015

(54) DETECTION OF AN AMPLIFICATION REACTION PRODUCT USING PH-SENSITIVE DYES

(71) Applicant: New England Biolabs, Inc., Ipswich, MA (US)

(72) Inventors: Nathan Tanner, Peabody, MA (US); Yinhua Zhang, North Reading, MA (US); Thomas C. Evans, Topsfield, MA (US)

(73) Assignee: New England Biolabs, Inc., Ipswich, MA (US)

( * ) Notice: Subject to any disclaimer, the term of this patent is extended or adjusted under 35 U.S.C. 154(b) by 0 days.

(21) Appl. No.: 13/799,995

(22) Filed: Mar. 13, 2013

(65) Prior Publication Data

US 2014/0057268 A1     Feb. 27, 2014

Related U.S. Application Data

(60) Provisional application No. 61/692,500, filed on Aug. 23, 2012, provisional application No. 61/722,830, filed on Nov. 6, 2012.

(51) Int. Cl.
| | | |
|---|---|---|
| *C12P 19/34* | (2006.01) | |
| *G01N 21/80* | (2006.01) | |
| *G01N 21/64* | (2006.01) | |
| *C12Q 1/68* | (2006.01) | |

(52) U.S. Cl.
CPC ............ *G01N 21/80* (2013.01); *G01N 21/6486* (2013.01); *C12Q 1/6844* (2013.01)

(58) Field of Classification Search
CPC ........... C12Q 1/6844; C12Q 2527/119; C12Q 2563/107; G01N 21/6486; G01N 21/80
USPC ................................ 435/91.2, 6.12
See application file for complete search history.

(56) References Cited

U.S. PATENT DOCUMENTS

| | | | |
|---|---|---|---|
| 7,888,015 B2 | 2/2011 | Toumazou et al. | |
| 2004/0197803 A1 | 10/2004 | Yaku et al. | |
| 2004/0209275 A1* | 10/2004 | Liew et al. ......................... | 435/6 |
| 2008/0032295 A1 | 2/2008 | Toumazou et al. | |
| 2010/0209973 A1* | 8/2010 | Kim et al. ..................... | 435/91.2 |
| 2011/0262903 A1 | 10/2011 | Davidson et al. | |

FOREIGN PATENT DOCUMENTS

| | | | |
|---|---|---|---|
| WO | WO 2010107816 | | 9/2010 |
| WO | WO 2011039425 | * | 7/2011 |

OTHER PUBLICATIONS

Notomi, et al., Nucleic Acids Research, 28:E63 (2000).
Gill, et al., Nucleosides, Nucleotides and Nucleic Acids, 27:224-243 (2008).
Kim, et al., Bioanalysis, 3:227-39 (2011).
Mori, et al., Biochem Biophys res Commun, 289:150-4 (2001).
Ganddelman, et al., PLoS One 5:e14155 (2010).
Tomita, et al., Nat Protoc, 3:877-82 (2008).
Nagamine, et al., Clin Chem, 47:1742-3 (2001).
Nagamine, et al., Mol. Cell. Probes, 16:223-229 (2002).
Goto, et al., BioTechniques 46:167-172 (2009).
Invitrogen BCECF [available online] Apr. 24, 2006 [retrieved Nov. 26, 2013]. Available on the internet [click on manuals and protocols: ,URL: http://www.lifetechnologies.com/order/catalog/product/B1151>.
International Search Report for PCT/US2013/056046 dated Dec. 13, 2013.

* cited by examiner

*Primary Examiner* — Cynthia B Wilder
(74) *Attorney, Agent, or Firm* — New England Biolabs, Inc; Harriet M. Strimpel

(57) ABSTRACT

Methods are provided for a rapid, low cost approach to monitoring an amplification reaction. This includes monitoring the progress of isothermal or PCR amplification reactions to completion using pH-sensitive dyes that are either colored or fluorescent. Compositions are described that include a mixture of a DNA polymerase, deoxyribonucleotide triphosphate and a weak buffer of less than 1 mM Tris or equivalent or no buffer.

14 Claims, 13 Drawing Sheets
(7 of 13 Drawing Sheet(s) Filed in Color)

SEQUENCE LISTING

```
<160> NUMBER OF SEQ ID NOS: 34

<210> SEQ ID NO 1
<211> LENGTH: 42
<212> TYPE: DNA
<213> ORGANISM: Enterobacteria phage lambda

<400> SEQUENCE: 1
cgaactgttt cgggattgca ttctggaact ccaaccatcg ca                 42

<210> SEQ ID NO 2
<211> LENGTH: 43
<212> TYPE: DNA
<213> ORGANISM: Enterobacteria phage lambda

<400> SEQUENCE: 2
ggagcctgca taacggtttc gtcgactcaa tgctcttacc tgt                43

<210> SEQ ID NO 3
<211> LENGTH: 21
```

<212> TYPE: DNA
<213> ORGANISM: Enterobacteria phage lambda

<400> SEQUENCE: 3
gttggtcact tcgacgtatc g         21

<210> SEQ ID NO 4
<211> LENGTH: 20
<212> TYPE: DNA
<213> ORGANISM: Enterobacteria phage lambda

<400> SEQUENCE: 4
gctcgccgac tcttcacgat         20

<210> SEQ ID NO 5
<211> LENGTH: 18
<212> TYPE: DNA
<213> ORGANISM: Enterobacteria phage lambda

<400> SEQUENCE: 5
tttgcagacc tctctgcc         18

<210> SEQ ID NO 6
<211> LENGTH: 20
<212> TYPE: DNA
<213> ORGANISM: Enterobacteria phage lambda

<400> SEQUENCE: 6
ggatttttta tatctgcaca         20

<210> SEQ ID NO 7
<211> LENGTH: 44
<212> TYPE: DNA
<213> ORGANISM: Caenorhabditis elegans

<400> SEQUENCE: 7
gattccactt ccaacgtcgt tgcataggca ttgtatccag agtg         44

<210> SEQ ID NO 8
<211> LENGTH: 42
<212> TYPE: DNA
<213> ORGANISM: Caenorhabditis elegans

<400> SEQUENCE: 8
cgaagtgaac cttgtcaaca tgagactacc cacatcgtta cc         42

<210> SEQ ID NO 9
<211> LENGTH: 20
<212> TYPE: DNA
<213> ORGANISM: Caenorhabditis elegans

<400> SEQUENCE: 9
agcaacatag gtttcagttc         20

<210> SEQ ID NO 10
<211> LENGTH: 18
<212> TYPE: DNA
<213> ORGANISM: Caenorhabditis elegans

<400> SEQUENCE: 10
ctgtgaacgg tcatcacc         18

<210> SEQ ID NO 11

```
<211> LENGTH: 20
<212> TYPE: DNA
<213> ORGANISM: Caenorhabditis elegans

<400> SEQUENCE: 11
acggacatgt cgatcatgga                                                 20

<210> SEQ ID NO 12
<211> LENGTH: 22
<212> TYPE: DNA
<213> ORGANISM: Caenorhabditis elegans

<400> SEQUENCE: 12
cgtctccctt caatccgatg gc                                              22

<210> SEQ ID NO 13
<211> LENGTH: 45
<212> TYPE: DNA
<213> ORGANISM: Homo sapiens

<400> SEQUENCE: 13
atccccagtc tgtgaaattg ggcaaaatgc tgggattata gatgt                     45

<210> SEQ ID NO 14
<211> LENGTH: 47
<212> TYPE: DNA
<213> ORGANISM: Homo sapiens

<400> SEQUENCE: 14
gcagcagaaa gattattaac ttgggcagtt ggtaagtaaa tggaaga                   47

<210> SEQ ID NO 15
<211> LENGTH: 19
<212> TYPE: DNA
<213> ORGANISM: Homo sapiens

<400> SEQUENCE: 15
tccttgaact ttggtctcc                                                  19

<210> SEQ ID NO 16
<211> LENGTH: 23
<212> TYPE: DNA
<213> ORGANISM: Homo sapiens

<400> SEQUENCE: 16
cagttcataa aggaattgat agc                                             23

<210> SEQ ID NO 17
<211> LENGTH: 20
<212> TYPE: DNA
<213> ORGANISM: Homo sapiens

<400> SEQUENCE: 17
agaaccagag gccaggcgag                                                 20

<210> SEQ ID NO 18
<211> LENGTH: 22
<212> TYPE: DNA
<213> ORGANISM: Homo sapiens

<400> SEQUENCE: 18
aggcagatag gcttagactc aa                                              22
```

```
<210> SEQ ID NO 19
<211> LENGTH: 48
<212> TYPE: DNA
<213> ORGANISM: Homo sapiens

<400> SEQUENCE: 19
ccaaagagta aagtccttct ctctcgagag actgttggcc cttgaagg          48

<210> SEQ ID NO 20
<211> LENGTH: 47
<212> TYPE: DNA
<213> ORGANISM: Homo sapiens

<400> SEQUENCE: 20
gtgttgatgt tatccacctt ttgtggacta ggaaaacaga tcaatag           47

<210> SEQ ID NO 21
<211> LENGTH: 20
<212> TYPE: DNA
<213> ORGANISM: Homo sapiens

<400> SEQUENCE: 21
taatcctgga actccggtgc                                         20

<210> SEQ ID NO 22
<211> LENGTH: 23
<212> TYPE: DNA
<213> ORGANISM: Homo sapiens

<400> SEQUENCE: 22
tttatgccaa ttaacatttt gac                                     23

<210> SEQ ID NO 23
<211> LENGTH: 19
<212> TYPE: DNA
<213> ORGANISM: Homo sapiens

<400> SEQUENCE: 23
atccacaggg aggagctct                                          19

<210> SEQ ID NO 24
<211> LENGTH: 19
<212> TYPE: DNA
<213> ORGANISM: Homo sapiens

<400> SEQUENCE: 24
ctccacctat aaaatcggc                                          19

<210> SEQ ID NO 25
<211> LENGTH: 44
<212> TYPE: DNA
<213> ORGANISM: pAII17 plasmid

<400> SEQUENCE: 25
aaaatccagc gcatgggcgc ggcgttcgcg gttgaagtca aggg              44

<210> SEQ ID NO 26
<211> LENGTH: 44
<212> TYPE: DNA
<213> ORGANISM: pAII17 plasmid

<400> SEQUENCE: 26
cgcttcgtgg attaccagct tttctggcgg tacttcgtac ttgc              44
```

```
<210> SEQ ID NO 27
<211> LENGTH: 47
<212> TYPE: DNA
<213> ORGANISM: Homo sapiens

<400> SEQUENCE: 27
accgcatcga atgcatgtct cgggcaaaat gctgggatta tagatgt          47

<210> SEQ ID NO 28
<211> LENGTH: 46
<212> TYPE: DNA
<213> ORGANISM: Homo sapiens

<400> SEQUENCE: 28
ggattccgct ccagacttct cgggcagttg gtaagtaaat ggaaga           46

<210> SEQ ID NO 29
<211> LENGTH: 19
<212> TYPE: DNA
<213> ORGANISM: Homo sapiens

<400> SEQUENCE: 29
tccttgaact ttggtctcc                                         19

<210> SEQ ID NO 30
<211> LENGTH: 23
<212> TYPE: DNA
<213> ORGANISM: Homo sapiens

<400> SEQUENCE: 30
cagttcataa aggaattgat agc                                    23

<210> SEQ ID NO 31
<211> LENGTH: 24
<212> TYPE: DNA
<213> ORGANISM: pAII17 plasmid

<400> SEQUENCE: 31
agcggggagg aagggagtaa agtt                                   24

<210> SEQ ID NO 32
<211> LENGTH: 25
<212> TYPE: DNA
<213> ORGANISM: Escherichia coli

<400> SEQUENCE: 32
cagtatcaga tgcagttccc aggtt                                  25

<210> SEQ ID NO 33
<211> LENGTH: 45
<212> TYPE: DNA
<213> ORGANISM: Escherichia coli

<400> SEQUENCE: 33
ctggcccacg agggcgaaga ggcaggcacc ggcccgatcc tgatg            45

<210> SEQ ID NO 34
<211> LENGTH: 44
<212> TYPE: DNA
```

```
<213> ORGANISM: Escherichia coli

<400> SEQUENCE: 34
cgccgcgccc atgcgctgga ttttcggttc ggagccgtca cggc                    44
```

DETECTION OF AN AMPLIFICATION REACTION PRODUCT USING PH-SENSITIVE DYES

CROSS REFERENCE

This application claims right of priority to provisional patent application Ser. No. U.S. 61/692,500 filed Aug. 23, 2012 and provisional patent application Ser. No. U.S. 61/722, 830 filed Nov. 6, 2012.

BACKGROUND OF THE INVENTION

Sequence-specific isothermal and polymerase chain reaction (PCR) nucleic acid amplification techniques represent rapidly growing sectors of molecular diagnostics, offering rapid, sensitive detection of DNA samples.

Electrophoresis is a traditional method of detecting DNA products in a post-amplification step that utilizes labor intensive manual processing and instrumentation. Recent developments in isothermal amplification has provided alternative detection methods, for example, fluorescence detection of double-stranded DNA (dsDNA) with an intercalating or magnesium-sensitive fluorophore (Notomi, et al., *Nucleic Acids Res.*, 28:E63 (2000); Tomita, et al., *Nat. Protoc.*, 3:877-82 (2008); Goto, et al., *BioTechniques*, 46:167-72, (2009)); bioluminescence through pyrophosphate conversion (Gandelman, et al., *PLoS One*, 5:e14155 (2010); or turbidity detection of precipitated magnesium pyrophosphate (Mori et al., *Biochem. Biophys. Res. Commun.*, 289:150-4 (2001)). However, these visual methods typically require long incubation times (>60 minutes), require specific instruments for detection, or are too subtle in change for robust detection outside of the laboratory. Advances in real time PCR equipment and chemistries have allowed monitoring many samples simultaneously during the PCR reaction. The detecting principles are typically based on either using fluorescence detection of dsDNA with an intercalating dye or using sequence-specific fluorescent probes requiring costly instruments. Alternatively, instruments have been developed for detecting hydrogen ions released during polymerase dependent amplification. Detection of these hydrogen ions has been achieved using sophisticated electronic detection and microfluidic devices, for example as demonstrated in U.S. Pat. No. 7,888, 015 for use in high-throughput Next Generation Sequencing (Ion Torrent™ Sequencing, Life Technologies, Grand Island, N.Y.).

Point-of-care and field diagnostics require rapid and simple tests, ideally detecting target nucleic acid in less than 30 minutes and without sophisticated and costly equipment.

SUMMARY

In an embodiment of the invention, a preparation is provided that includes a pH-sensitive dye, a DNA polymerase, dNTPs, in a formulation that contains a weak buffering agent in an amount of less than 1 mM Tris or equivalent or no buffering agent.

In one aspect, the preparation includes one or more of primers; and a template DNA. In another aspect, the pH sensitive dye is either a visually detectable color dye or a fluorescent dye.

In one embodiment of the invention, a method is provided for detecting amplification of a nucleic acid that includes: providing an amplification reaction mixture containing a template DNA; a DNA polymerase and a pH-sensitive dye in a weakly-buffered or a non-buffered solution; and detecting a change in spectral properties of the dye resulting from amplification of the target DNA.

In one aspect, the nucleic acid amplification is an isothermal amplification or a PCR.

In another aspect, the isothermal nucleic acid amplification is selected from the group consisting of a loop-mediated isothermal amplification (LAMP), a helicase displacement amplification (HDA), a strand displacement amplification (SDA), a recombinase polymerase amplification (RPA) and a nicking enzyme amplification reaction (NEAR).

In one aspect, the pH sensitive dye is soluble and in another aspect, the soluble dye is a colored dye detectable in visible light. Examples of a suitable dye are cresol red, phenol red, m-cresol purple, bromocresol purple, neutral red, naphtholphthalein, thymol blue, naphtolphthalein.

In another aspect, the pH sensitive dye is a fluorescent dye for example, 2',7'-Bis-(2-Carboxyethyl)-5-(and-6)-Carboxyfluorescein or a carboxyl seminaphthorhodafluor.

In another aspect, the weakly buffered solution contains less than 1 mM of Tris buffer or equivalent buffer.

In another aspect of the method, detecting amplification relies on comparing a change in spectral or fluorescent properties of the dye before and after amplification has occurred.

In one embodiment of the invention, a method is provided for monitoring a nucleic acid amplification of a target sequence if present in the sample, where a change of pH is determined in the presence of the target sequence as amplification proceeds beyond a threshold number of cycles, the monitoring being achieved by adding a pH-sensitive color or fluorescent dye to the reaction mixture; and determining a change in color prior to amplification compared with when amplification has occurred.

BRIEF DESCRIPTION OF THE FIGURES

The patent or application file contains at least one figure executed in color. Copies of this patent or patent application publication with color figures will be provided by the Office upon request and payment of the necessary fee.

FIG. 1A shows the color of samples at the start of the reaction in the presence of phenol red, cresol red, neutral red, and m-cresol purple at 50 μM or 100 μM.

FIG. 1B shows the color of samples after a 30 minute LAMP reaction at 65° C. in response to decreasing pH resulting from amplification when Bst 2.0 (New England Biolabs, Ipswich, Mass.) DNA polymerase was included in the reaction mixture but not when it was omitted. Samples turned from red to yellow in the presence of phenol red and cresol red; from colorless to red using neutral red; and from violet to yellow with m-cresol purple.

FIG. 2A shows the color of samples at the start of the reaction. The dyes used here are higher alkalinity indicators (thymol blue, naphtholphthalein, phenolphthalein) at pH 10, or more neutral indicator (bromocresol purple) at pH 7.5, all included at 50 μM or 100 μM as shown.

FIG. 2B shows the color of samples after 60 minute LAMP reactions at 65° C. in response to decreasing pH resulting from amplification when Bst 2.0 DNA polymerase was included in the reaction mixture but not when it was omitted. Samples containing Bst 2.0 turned from blue to yellow in the presence of thymol blue; blue to colorless (50 uM) or light blue (100 uM) in the presence of naphtholphthalein; pink to colorless (50 uM) or light pink (100 uM) in the presence of phenolphthalein; and violet to yellow in the presence of bromocresol purple.

Reactions that contained Bst 2.0 DNA polymerase and target genomic DNA (+Temp) or non-template control (NTC) and an indicator dye (Phenol red, Cresol Red, Neutral red or m-Cresol Purple) at 100 μM were incubated for (a) 0 minutes, (b) 15 minutes or (c) 60 minutes at 65° C.

Figure 1:
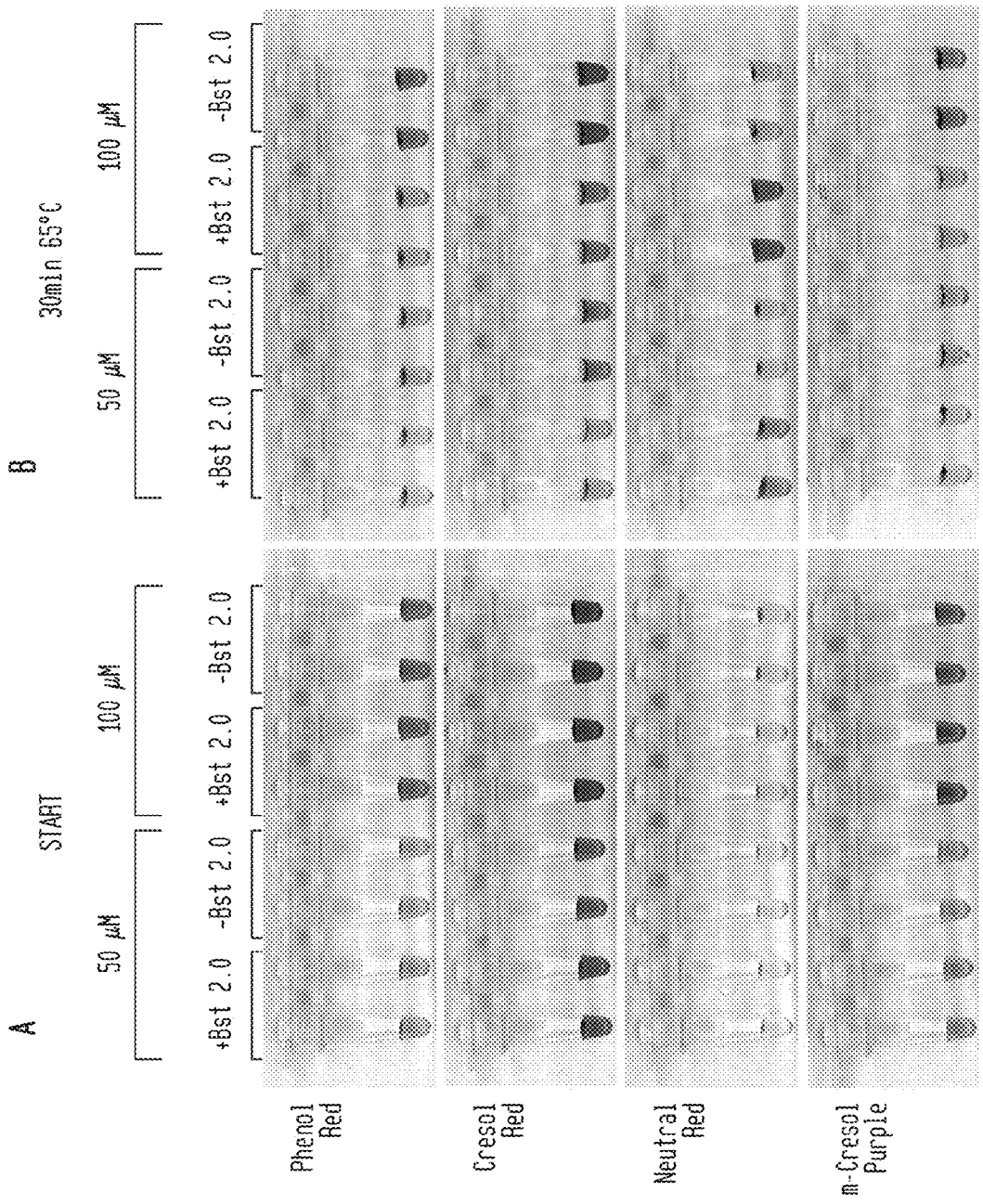
FIGS. 1A and 1B show visible color change detection of a completed amplification reaction using various indicator dyes. Here, LAMP is used to amplify lambda phage DNA target sequence in a low buffer solution at pH 9 such that at completion of amplification, the pH is reduced and a color change occurs.
Figure 2:
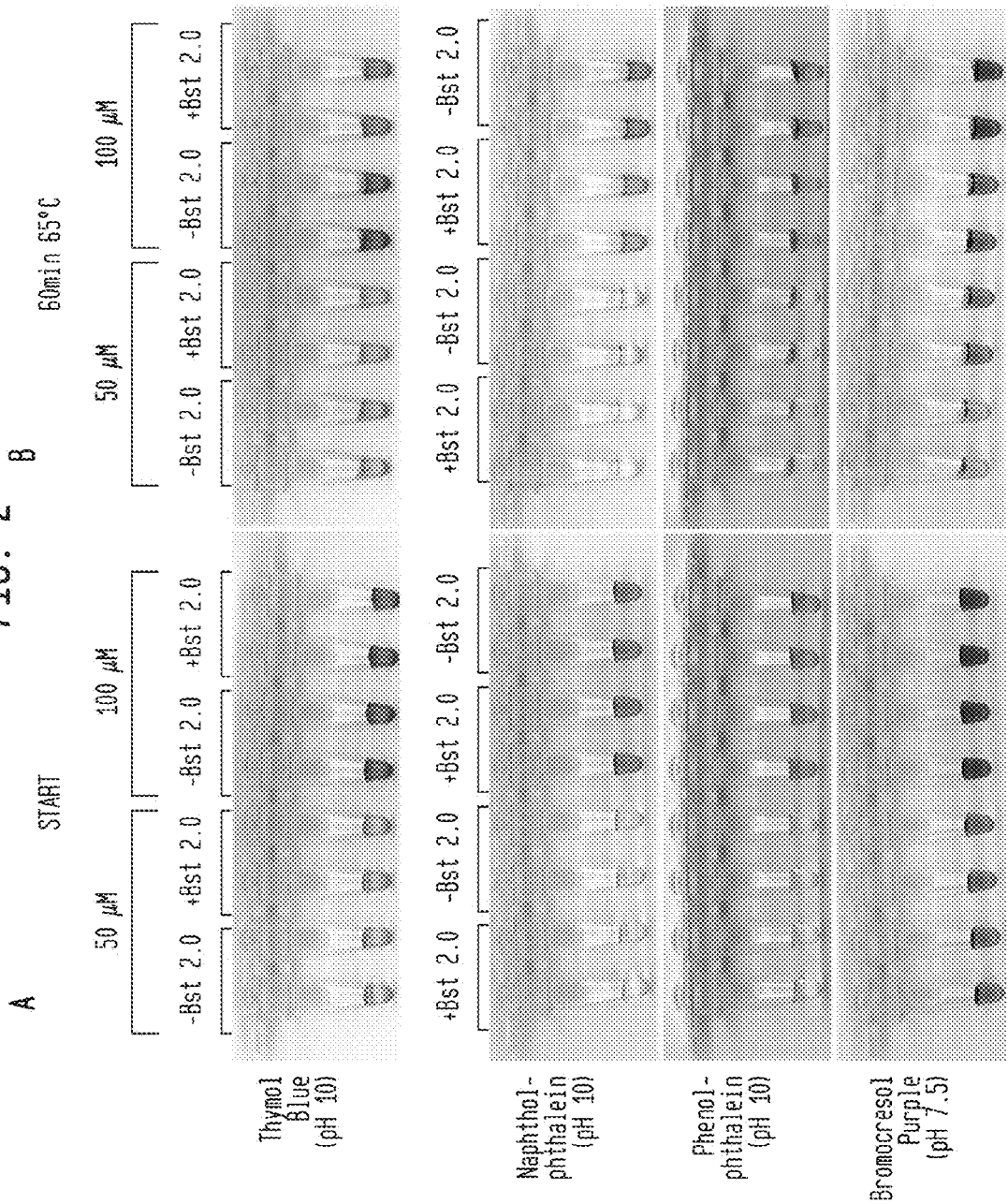
FIGS. 2A and 2B show a comparison of dye color before and after an amplification reaction. A lambda phage DNA target was amplified using LAMP in a low buffer solution at an initial pH 10 or pH 7.5 as indicated such that a color change occurs at completion of the amplification reactions.
Figure 3:
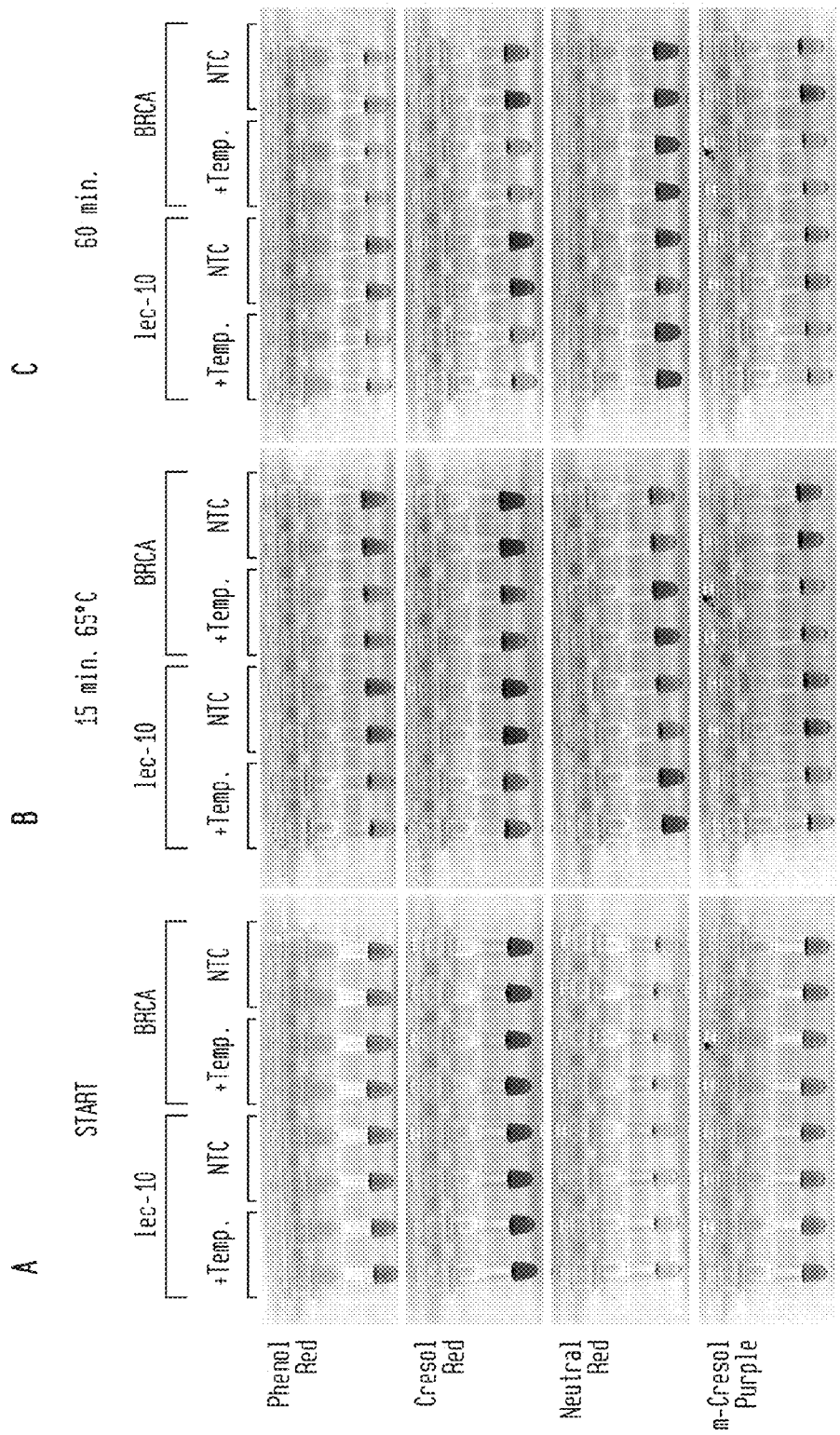
FIG. 3A-C shows that color change detection in an amplification reaction is specific to amplification of target DNA. Here two different DNAs were shown to respond similarly when amplified. LAMP reactions were performed in low buffer reaction solutions with primers for either *C. elegans* lec-10 or human BRCA1 sequence targets as indicated.

FIG. 3A shows that all tubes of a particular indicator started at the same color at time=0 minutes.

FIG. 3B shows that only samples containing template DNA changed color at 15 minutes after initiation of amplification, denoting positive amplification of target DNA.

FIG. 3C shows that the color change of amplified samples containing template DNA had intensified at 60 minutes after initiation of amplification. Some NTC showed intermediate levels of color change due to non-specific amplification, though clearly distinguished temporally from positive (target) amplification.

Figure 4:
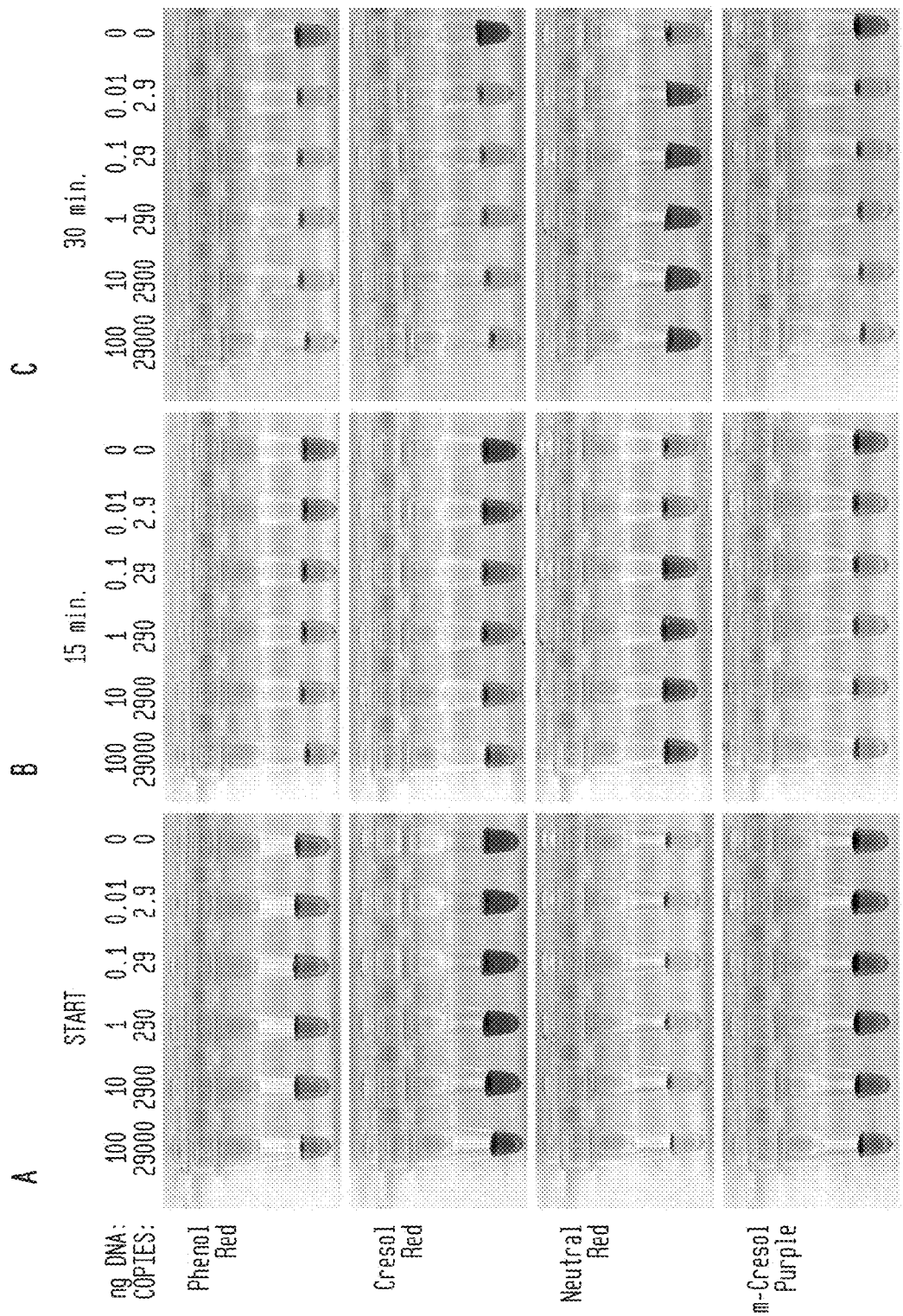

FIG. 4A-C shows sensitivity of color change over reaction time in response to template amount during amplification with four pH-sensitive dyes.

LAMP reactions were performed in low buffer reaction solution with primers for human CFTR sequence using a serial 10 fold titration of template DNA (HeLa) (100 ng–0.1 ng or 0.01 ng) as indicated.

FIG. 4A shows the color of the indicator dyes (100 μM each) at Time=0 minutes.

FIG. 4B shows a color change at time=15 minutes after amplification of 100 ng–0.1 ng target DNA using phenol red and neutral red dyes, and 100 ng–0.01 ng DNA for cresol red and m-cresol purple dyes.

FIG. 4C shows the same reactions as in FIGS. 4A and 4B at time=30 minutes where a complete color change was observed for all template amounts for all dyes, while all non-template controls retained the initial color.

Figure 5:
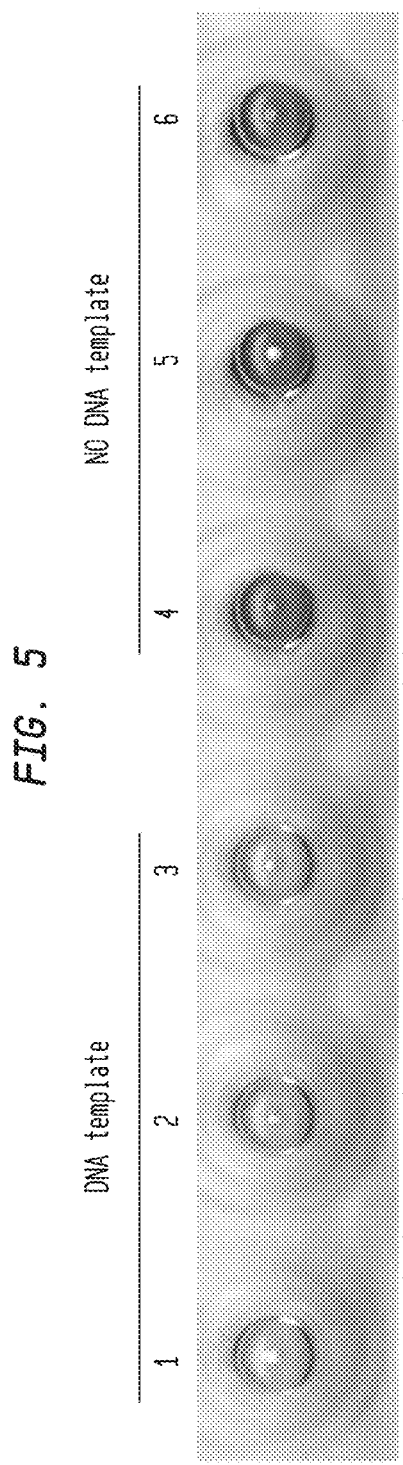

FIG. 5 shows the detection of a PCR amplification reaction using 100 μM phenol red in a low buffer reaction. Only the triplicate reactions (labeled 1, 2 and 3) that contained DNA template changed color from pink to yellow while the reactions without DNA template (4, 5, and 6) remained pink.

Figure 6:
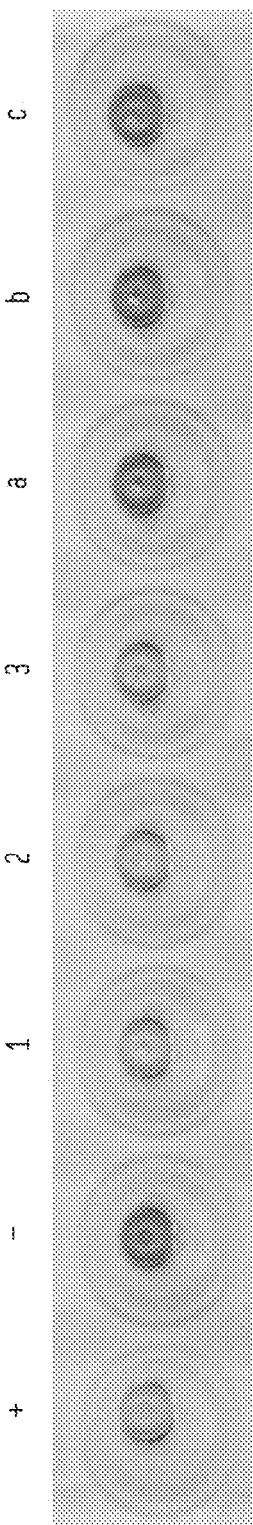

FIG. 6 shows identification of specific plasmid DNA in bacterial colonies by using PCR reactions containing 100 μM phenol red. After PCR, positive samples (1-3) with bacteria from three colonies that contained the target plasmid changed color from pink to yellow. The three negative controls (a-c) that had bacteria from colonies containing an unrelated plasmid did not. This matched the result of positive (+) reactions with plasmid DNA and negative controls (−) with water only and demonstrated the applicability of color change detection for screening bacterial colonies for the presence of a particular plasmid.

Figure 7:
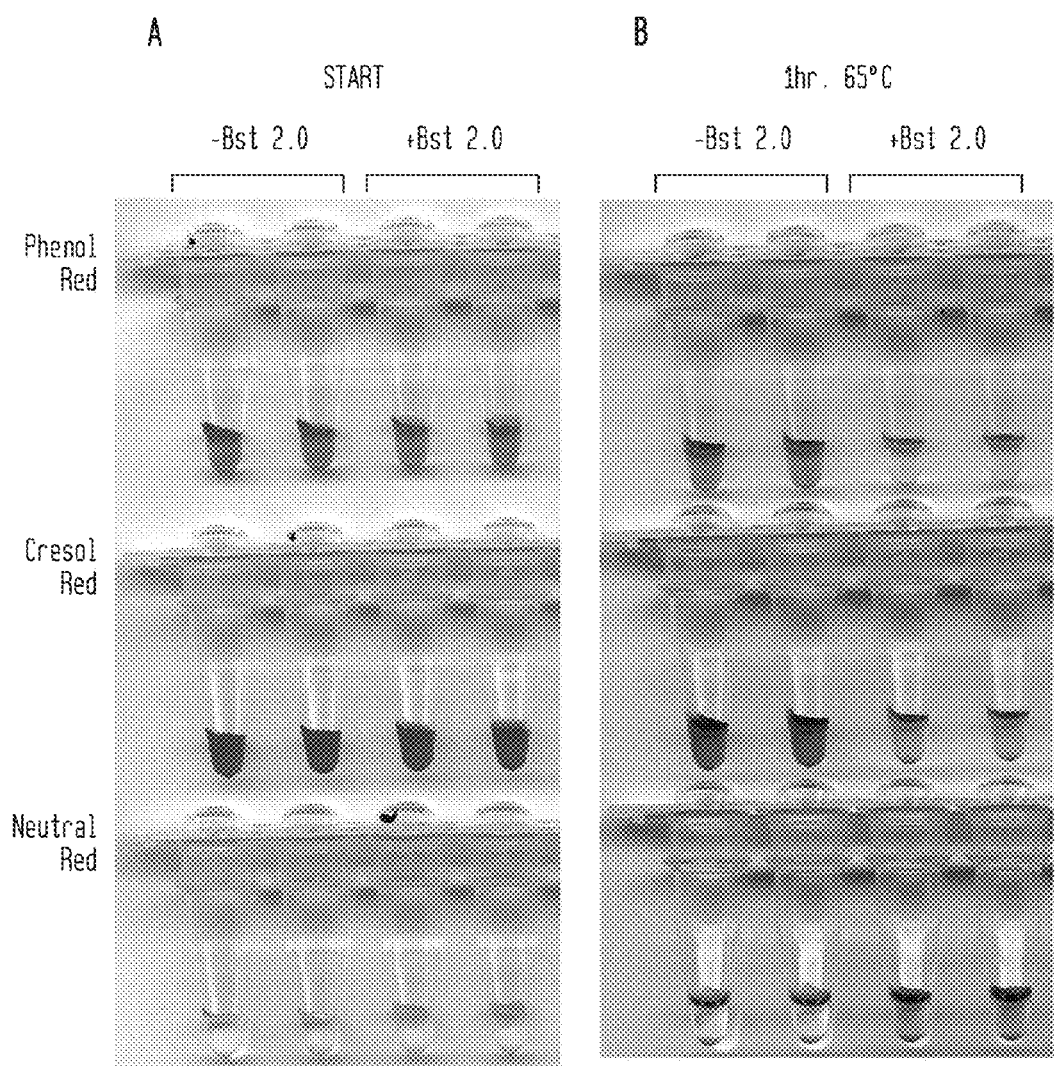

FIGS. 7A and 7B shows detection of SDA reactions for human DNA and primers for the BRCA1 gene using 100 μM visible pH indicators in the presence and absence of Bst 2.0 polymerase. A color change was observed in samples containing Bst 2.0 and no color change was observed in samples absent Bst 2.0.

FIG. 7A shows the colors of reactions in the presence or absence of Bst 2.0 at the start of the reaction.

FIG. 7B shows the colors of the reactions in the presence or absence of Bst 2.0 after 1 hour incubation at 65° C. Color change only occurred in the presence of polymerase, indicating detection of amplification.

Figure 8:
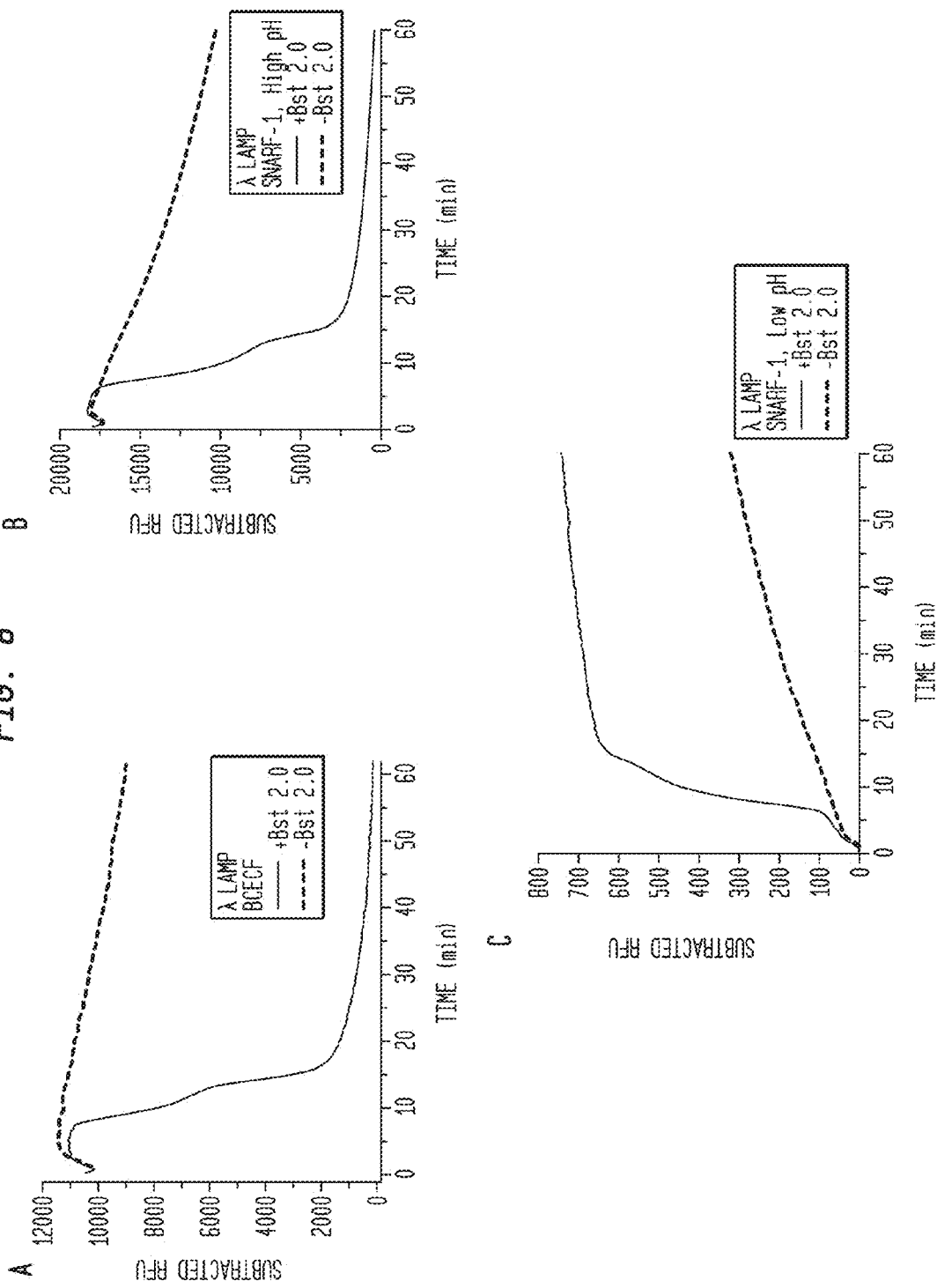

FIG. 8A-C shows the detection of LAMP reactions using real-time measurement of fluorescent pH indicators. Data was plotted as subtracted RFU, with a background value subtracted from final RFU (FIGS. 8A and 8B) or initial RFU (FIG. 8C) to produce a baseline (0 RFU). Without DNA polymerase, little fluorescence change was observed (dashed lines), showing that detection was specific to amplification and pH drift was minimal under isothermal conditions.

FIG. 8A shows a significant drop of fluorescence for BCECF-AM (measured in FAM channel of CFX96™ fluorimeter (Bio-Rad, Hercules, Calif.)) in the presence of Bst 2.0 DNA polymerase corresponding to a DNA amplification reaction.

FIG. 8B shows a drop in fluorescence for the high pH form of SNARF-1® (Life Technologies, Grand Island, N.Y.) (ROX channel) in response to DNA amplification FIG. 8C shows a gain in fluorescence for the low pH form of SNARF-1 (HEX channel) in response to DNA amplification.

Figure 9A:
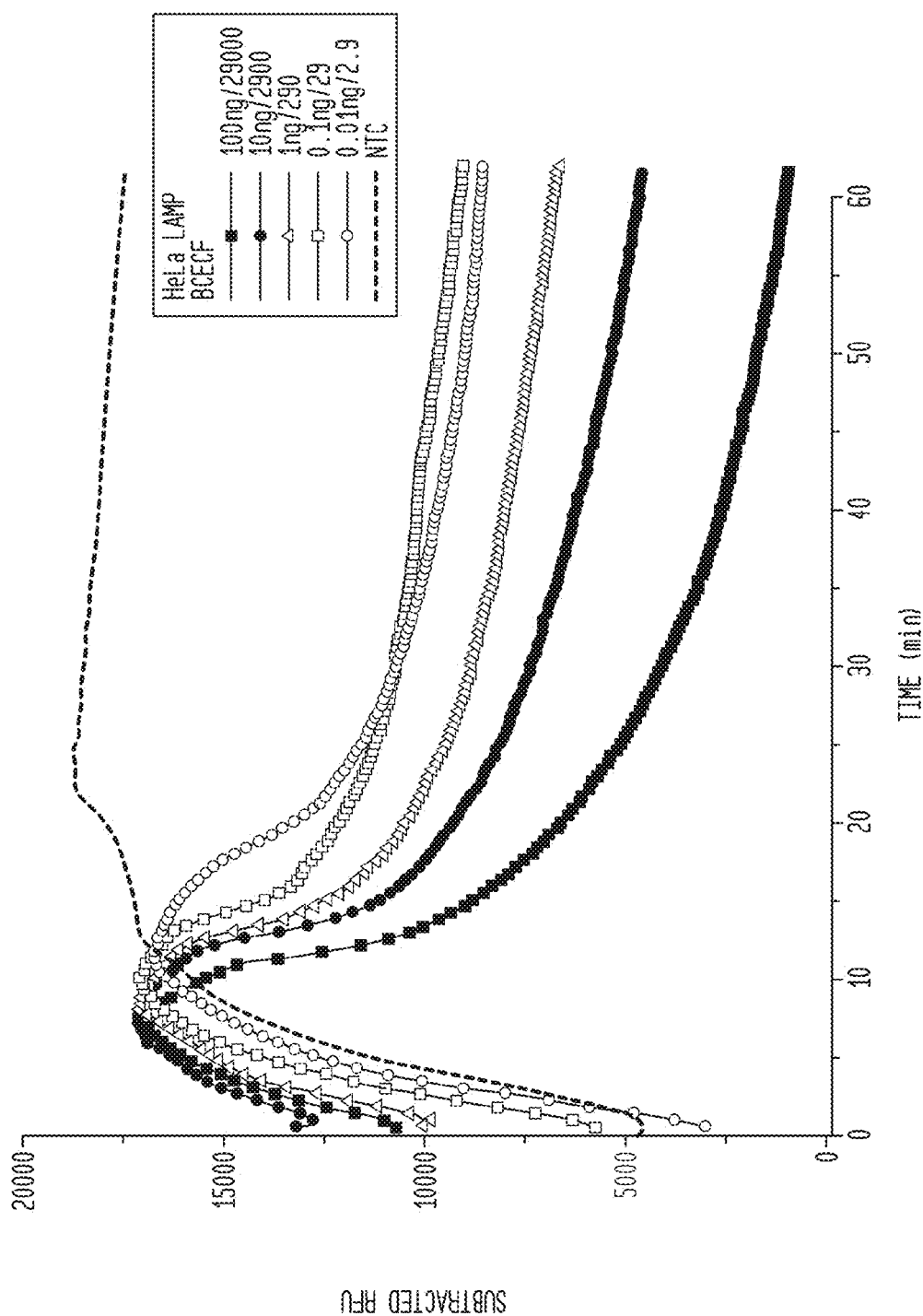
Figure 9B:
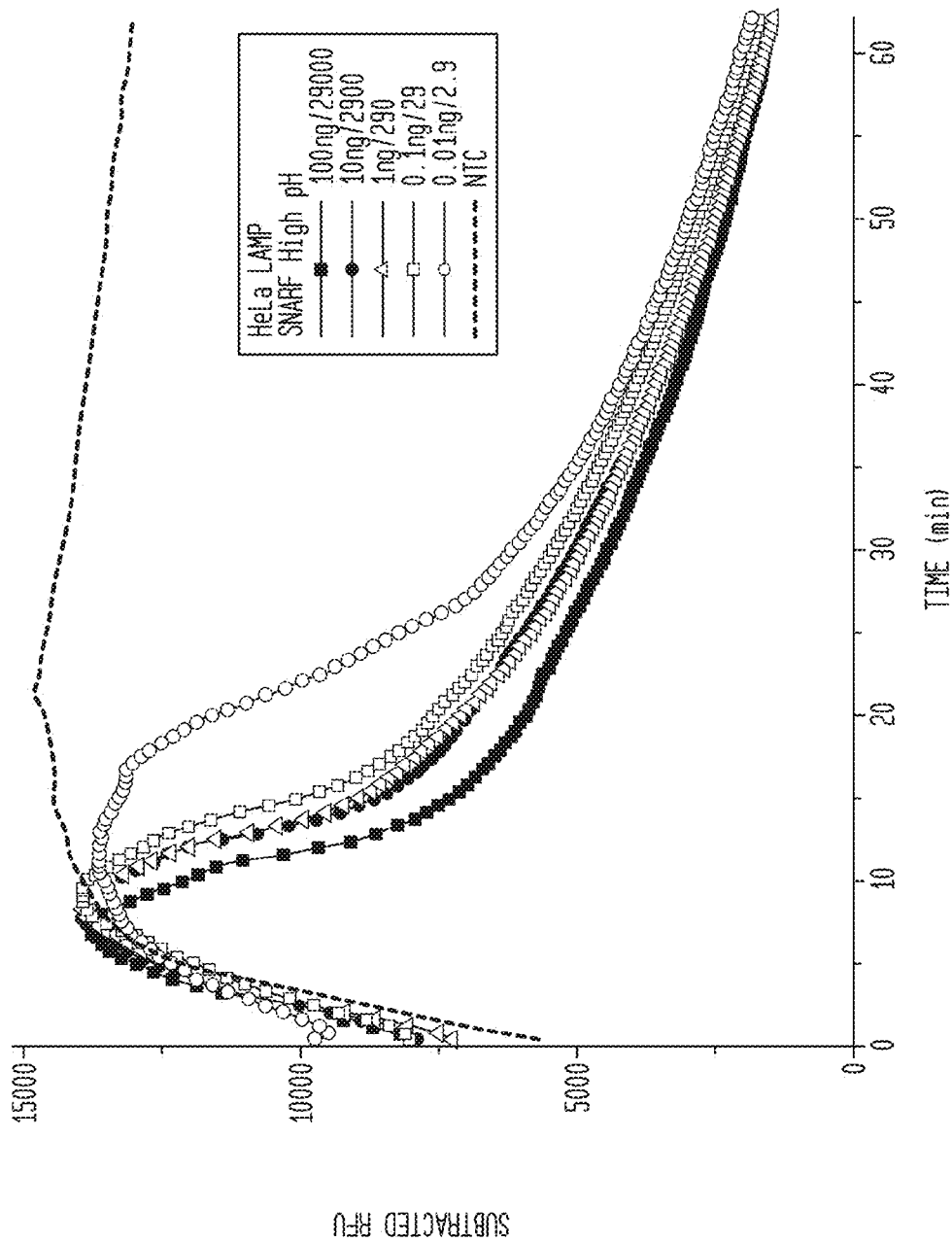
Figure 9C:
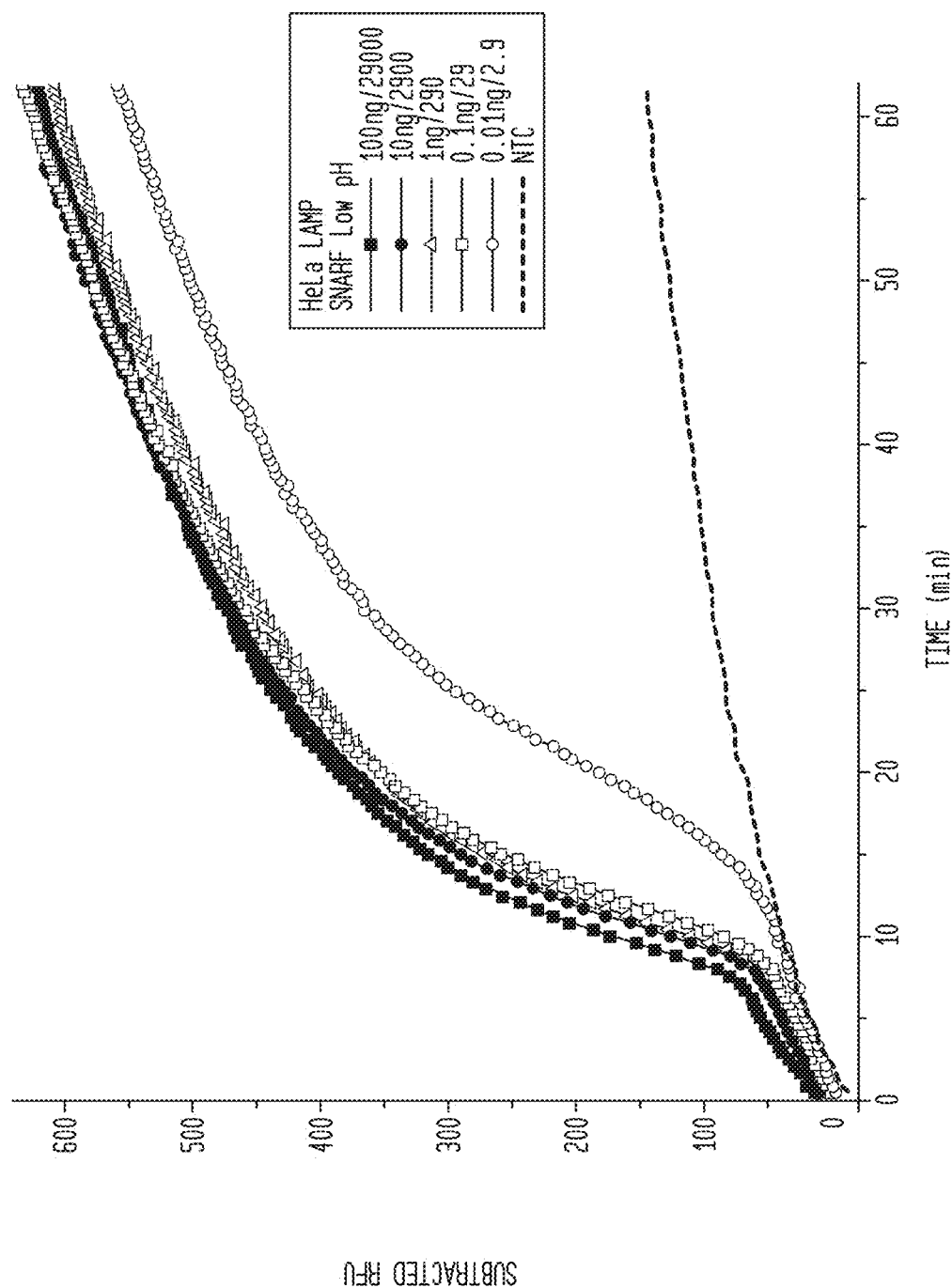

FIG. 9A-C shows the sensitivity of fluorescence detection of pH change in LAMP reactions. Reactions contained primers for human CFTR and varying amounts of template HeLa DNA as indicated. pH change was observed to be in a template concentration-dependent manner, where the time required for fluorescence change was correlated with the amount of template DNA present in the reaction. Higher template amounts produced more rapid pH change, and thus fluorescence change, and lower template amounts resulted in slower pH change, while the NTC remained stable at the initial pH and fluorescence value.

FIG. 9A shows a drop in fluorescence corresponding to a drop in pH for BCECF-AM during DNA amplification.

FIG. 9B shows a drop in fluorescence corresponding to a drop in pH for SNARF-1 (high pH) during DNA amplification.

FIG. 9C shows a gain in fluorescence of the low pH form of SNARF-1 during DNA amplification.

Figure 10A:
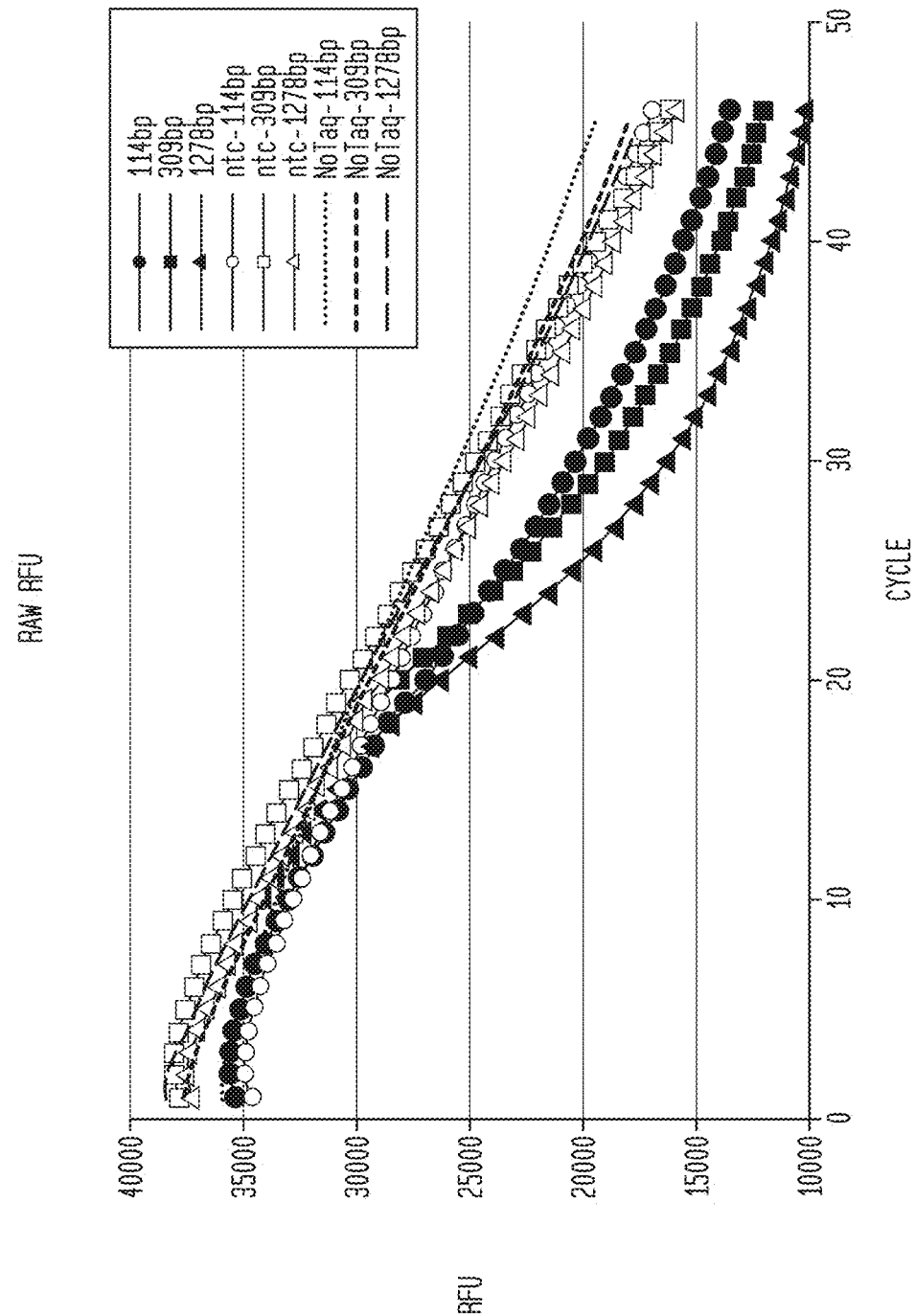
Figure 10B:
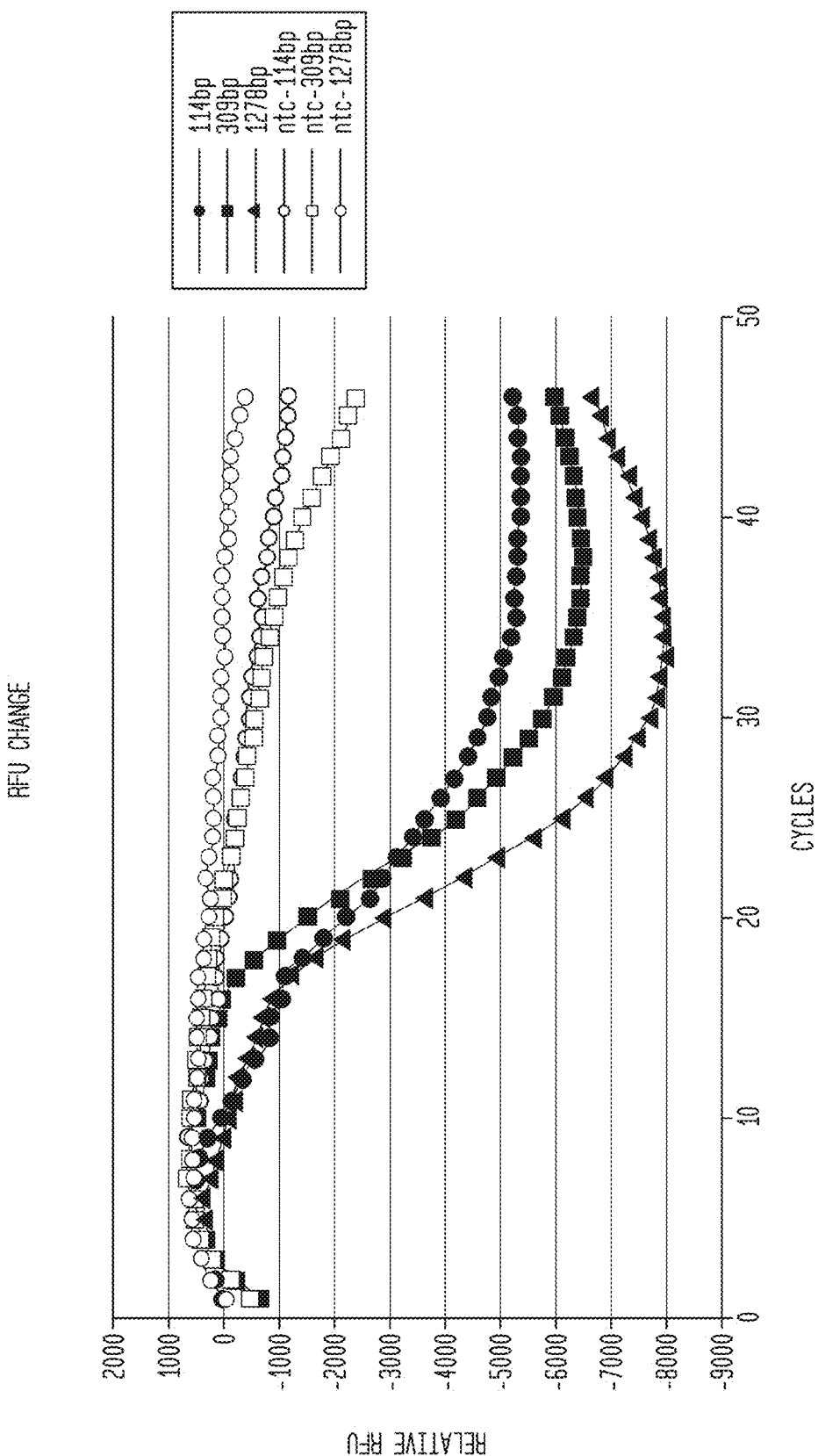

FIGS. 10A and 10B show the detection of the PCR reaction amplifying target DNA of different sizes using SNARF-1. Three fragments with different sizes (114 bp, 308 bp, 1278 bp) were amplified. The presence of template DNA in the reaction led to the significant change of fluorescence reading during PCR (>5000 RFU above background change). The level of signal drop was proportional to the amplicon size, with ~5000 RFU decrease for 114 bp, 6000 RFU for 300 bp, and 8000 RFU for the 1278 bp amplicon. All amplicons resulted in a threshold time for background-corrected fluorescence drop of ~20 cycles.

FIG. 10A shows raw, uncorrected RFU recorded over PCR cycling.

FIG. 10B shows net RFU change during the PCR cycling after subtracting signal from tubes without Taq DNA polymerase to correct for background pH and fluorescence drop due to thermal cycling of PCR reaction.

DESCRIPTION OF EMBODIMENTS

Nucleoside triphosphate incorporation events during DNA synthesis generate a pyrophosphate group as well as a hydrogen ion during reactions catalyzed by a DNA polymerase.

Without buffering conditions, protons accumulate in a DNA amplification reaction so that the solution becomes increasingly acidic with increasing DNA amplification.

Despite initial concerns that pH indicator dyes, which were large bulky organic molecules might interfere with the amplification reaction, or that the increase in proton concentration during amplification was not sufficient to permit a detectable change in color or fluorescence in a pH indicator, it was shown that these molecules could be used to monitor DNA amplification. pH change was observed to be as high as 4 pH units in LAMP reactions despite the buffering capacity of the solution, with buffering contributions from the dNTPs, nucleic acids, enzymes, and buffering agent carried over from storage solution. The utility of chemical and fluorescent dyes for monitoring amplification reactions is supported by a series of examples that are not intended to be limiting. The fluorescent dyes and also chemical dyes which include pH indicator dyes that are preferably visible by eye are effective in detection of the formation of amplification products at: various time points; varying concentration of dyes and DNA target; different types target DNAs and any type of amplification protocol utilizing a polymerase and nucleotides such as, for example, SDA, LAMP, and PCR analyzed both qualitatively and quantitatively. Significantly, the detection of the amplification endpoint could be accomplished without ambiguity.

Embodiments of the invention provide compositions and methods that rapidly and reliably detect formation and optionally the quantity of amplification products at low cost and with robust efficiency using a wide range of pH-sensitive visible or fluorescent dyes individually or together which serve as a means to detect DNA amplification. Since polymerases typically operate at a pH of 5-10, the choice of dyes reflect changes within this range. For visible dyes, a change of color is identified at different pHs whereas for fluorescent dyes, an increase or decrease of fluorescence may be detected as the pH is reduced depending on well-known properties of the fluorescent dye (see for example, BCECF-AM vs. SNARF-1).

The pH of the amplification reaction may be reliably measured using indicator dyes in the absence of a reaction buffer and also in the presence of some residual buffer (for example, up to, at least about 1 mM buffer, for example 150 μM Tris) such as might arise when carried over from the enzyme storage buffer. In one embodiment, a PCR reaction was performed using standard conditions either in the absence of reaction buffer or in the presence of residual buffer (150 μM Tris) with similar results.

Using a strand-displacing polymerase tolerant to pH range of at least pH 5-10, LAMP was performed in solutions with <1 mM buffering agent. By initiating the reaction in alkaline conditions (pH 8-10) in the presence of neutral pH range transition indicator, an initial high pH color was observed (see for example, Table 1). As amplification proceeded, the solution pH dropped substantially to a second, acidic pH (pH 5-7) in as little as 10 minutes resulting in a detectable color change. This color difference was easily visible by eye.

There are a wide range of pH color indicators with varying colors any of which are suitable for use in the present embodiments (e.g. violet to yellow, red to yellow, yellow to red). Examples of 8 different pH sensitive dyes are provided herein that change color at different pHs. These examples are not intended to be limiting.

The detection of changes in the spectral properties of indicator dyes can be achieved by their photochemical properties using for example, the eyes of the operator, a fluorimeter, or a spectrophotometer. The term "detecting" may be used interchangeably with the term "monitoring".

Suitable visible dyes include: Neutral Red, which has a clear-yellow color when pH is higher than 8 and a red color when pH is less than 6.8; Phenol Red, which has a red color when pH is higher than 8 and a yellow color when pH is less than 6.4; Cresol Red, which has a reddish-purple color when pH is higher than 8.8 and a yellow color when pH is less than 7.2; Thymol Blue, which has a blue color when pH is higher than 9.6 and a yellow color when pH is less than 8.0; Phenolphthalein, which has a fuchsia color when pH is higher than 10 and colorless when pH is less than 8.3; and Naphtholphthalein, which has a greenish color when pH is higher than 8.7 and a pale-reddish color when pH is less than 7.3. These properties for dyes used herein are summarized in Table 1.

| Indicator | High pH Color | pH Transition | Low pH Color |
|---|---|---|---|
| Bromocresol purple | Violet | 6.5-5.2 | Yellow |
| Neutral red | Clear-yellow | 8.0-6.8 | Red |
| Phenol red | Red | 8.2-6.8 | Yellow |
| Cresol red | Red | 8.8-7.2 | Yellow |
| Naptholphthalein | Blue | 8.8-7.3 | Clear-red |
| m-Cresol purple | Violet | 9.0-7.4 | Yellow |
| Thymol blue | Blue | 9.6-8.0 | Yellow |
| Phenolphthalein | Red | 10-8.0 | Red |

Other examples of pH indicators include: methyl yellow, methyl orange, bromophenol blue, naphthyl red, bromocresol green, methyl red, azolitmin, nile blue, thymolphthalein, alizarin yellow, salicyl yellow, nitramine. These indicators may transition outside the range of traditional DNA polymerase tolerances, but the principle of amplification detection may be applied to alternate detection methods with an indicator appropriate for desired pH range.

One class of dyes that require a detection device is fluorescent dyes. Like visual dyes mentioned above, pH-sensitive fluorescence dyes have different levels of fluorescence emission or a shift of peak emission wavelength at different pH. Both the change in brightness and the shift in peak absorption can be easily detected using systems that are equipped with proper filter sets.

Fluorescent dyes for use in embodiments of the invention include 5-(and-6) carboxy SNARF-1 which features a shift in fluorescence based on pH. At high pH (pH 9) SNARF-1 maximum absorbance/emission at $A_{max}$ 575 nm/$Em_{max}$ 650 nm. These values blue-shift significantly when the pH lowers, to $A_{max}$ 525/$Em_{max}$ 590. This fluorescence shift allows simultaneous monitoring of the two states of the dye, with one fluorescence channel matching the high pH form (shows fluorescence decrease with amplification, FIG. 5) and another channel the low pH form (fluorescence increase). We measured a 90% loss of fluorescence for the high pH form (measured in ROX channel of CFX96 instrument or 200% gain of fluorescence (HEX channel) upon pH drop from pH 10 to pH 6 calibration solution. Other suitable fluorescent dyes related to SNARF-1 have been developed for monitoring pH change, including SNARF-4F and SNARF-5F, SNAFRs, SNAFL, 5-(and-6)-carboxynaphthofluorescein, 6-JOE, Oregon Green® (Life Technologies, Grand Island, N.Y.). Other fluorescent pH indicators include 2',7'-bis-(2-carboxyethyl)-5-(and-6)-carboxyfluorescein, acetoxymethyl ester (BCECF-AM) (Life Technologies, Grand Island, N.Y.) which at pH 9 has a absorbance/emission profile of $A_{max}$ 500 nm/$Em_{max}$ 535 nm. It also features a spectral blueshift as pH drops, but the low pH form is much less efficient in excitation, and the effective readout is limited to the decrease in fluorescence from the high pH form. An approximately 80% reduction in fluorescence was measured for BCECF-AM (FAM channel of CFX96) from pH 10 to pH 6. BCECF is derived from fluorescein and a number of dyes related to fluorescein show similar sensitivity to pH change.

Visual and fluorescent dyes including those mentioned above can be chemically modified to have altered colorimetric properties in response to pH changes. These modification can create dyes that are either brighter or change color at a narrower pH range and thus allow a better detection.

Isothermal polymerase dependent amplification reactions such as LAMP and SDA, HDA, RPA and NEAR can be readily monitored by measuring pH change using visible and fluorescent dyes. For example, LAMP amplification, see for example, Gill, et al., *Nucleos. Nucleot. Nucleic Acids*, 27:224-43 (2008); Kim, et al, *Bioanalysis*, 3:227-39 (2011); Nagamine et al., *Mol. Cel. Probes*, 16:223-9 (2002); Notomi et al., *Nucleic Acids Res.*, 28:E63 (2000); and Nagamine et al., *Clin. Chem.*, 47:1742-3 (2001) which commonly utilizes a Bst 2.0 polymerase can be monitored by measuring concomitant pH changes that are detectable visually using chemical or fluorescent dyes.

Temperature cycling amplification protocols such as PCR can be monitored by pH changes using chemical or fluorescent dyes regardless of which polymerase is used in the amplification. PCR may utilize polymerase such as Q5® DNA polymerase, Phusion® DNA polymerase, OneTaq® (New England Biolabs, Ipswich, Mass. (Phusion is a registered trademark of Thermo Fisher Scientific, Waltham, Mass.)). These polymerases without exception amplify DNA with concomitant pH changes detected by dyes. Indeed, any suitable polymerase may be used to amplify DNA resulting in a release of protons that can then be detected using pH sensitive indicator dyes.

There are many applications of this DNA amplification detection method. It can be used as a means to indicate successful amplification reactions in standard molecular biology protocols, obviating the need of running gel electrophoresis. This detection can include indication of the presence or absence of desired DNA species, as in screening colonies for carrying a correct insert in a plasmid. Detection of species extends to diagnostic applications, as the presence or absence of specific DNA or RNA target species can be indicated by color change after cycling or incubation time. This is particularly suited to isothermal amplification methods such as LAMP in field or point-of-care testing. The rapidity and robustness of the color change enable efficient detection of diagnostic targets quickly without sophisticated equipment. Color or fluorescence change can be monitored in real time, allowing quantification of amount of target nucleic acid where such information is required, e.g. sequencing library preparation, transcription profiling, and load measurement.

This pH-dependent detection method can be used in other applications that require DNA synthesis such as DNA sequencing. Addition of each nucleotide will generate a proton and total protons generated in a pool of DNA causes the reaction to become acidic. This change in pH can be detected using pH-sensitive dyes. Interrogating one of the four dNTPs in turn would determine which base can be added and thus allow sequence assembly after multiple rounds of reactions.

Buffering agents typically provide stability to reaction mixtures and components for storage. The detection method described herein requires minimal to no buffering agent but also maintenance of desired pH (typically alkaline) for proper color change during amplification. Small amounts of buffering agent present from enzyme storage buffer or reaction solution may be sufficient for this purpose, or, alternatively reaction mixtures may be lyophilized to preserve stability for long periods of storage.

Embodiments of the invention provide a simple, robust, rapid, sensitive and cost effective means for visual detection of nucleic acid amplification.

All references cited herein are incorporated by reference.

EXAMPLES

Example 1

Detection of LAMP Amplification Using a pH-Sensitive Visual Dye

LAMP reactions were performed with a buffer-free reaction solution: 10 mM $(NH_4)_2SO_4$, 50 mM KCl, 8 mM $MgSO_4$, 1.4 mM dNTPs, 0.1% Tween-20, pH 7.5-10. Final buffer concentration was 0.026 mM-0.4 mM Tris from enzyme storage buffer carryover.

Reactions were performed with primers for lambda phage DNA amplicon and 5 ng of lambda DNA (FIG. 1A-B, FIG. 2A-B; New England Biolabs, Ipswich, Mass.). Reactions were incubated for 30-60 minutes at 65° C. with either 50 μM or 100 μM pH indicator as shown in the presence or absence of DNA polymerase (Bst 2.0). Color change occurred only in the presence of DNA polymerase, indicating that amplification produced sufficient pH drop for visual identification.

In FIG. 3A-C, LAMP reactions were performed in buffer-free reaction solution with primers for either *C. elegans* lec-10 or human BRCA1 sequence targets. Reactions contained 82.5 ng *C. elegans* DNA, 100 ng HeLa DNA (+Temp) or no (NTC) DNA. Reactions were incubated at 65° C. for 30 minutes in the presence of pH indicators with only samples containing template DNA displaying color change as observed by eye.

In FIG. 4A-C, reactions contained primers for human CFTR and various amounts of template HeLa genomic DNA (100 ng-0.01 ng; 29000-2.9 copies). Robust color change was observed for 100 ng-0.1 ng with all indicators, and all concentrations for cresol red and m-cresol purple template concentrations at 15 minutes. After 30 minutes, all indicators changed color for all template concentrations while the negative control (no template DNA) remained at the initial high pH color. LAMP primer sequences used were as follows:

```
Lambda FIP:
                                       (SEQ ID NO: 1)
CGAACTGTTTCGGGATTGCATTCTGGAACTCCAACCATCGCA Lambda BIP:
                                       (SEQ ID NO: 2)
GGAGCCTGCATAACGGTTTCGTCGACTCAATGCTCTTACCTGT Lambda F3:
                                       (SEQ ID NO: 3)
GTTGGTCACTTCGACGTATCG Lambda B3:
                                       (SEQ ID NO: 4)
GCTCGCCGACTCTTCACGAT Lambda LoopF:
                                       (SEQ ID NO: 5)
TTTGCAGACCTCTCTGCC Lambda LoopB:
                                       (SEQ ID NO: 6)
GGATTTTTTATATCTGCACA
```

-continued

C.elegans FIP:
(SEQ ID NO: 7)
GATTCCACTTCCAACGTCGTTGCATAGGCATTGTATCCAGAGTG

C.elegans BIP:
(SEQ ID NO: 8)
CGAAGTGAACCTTGTCAACATGAGACTACCCACATCGTTACC

C.elegans F3:
(SEQ ID NO: 9)
AGCAACATAGGTTTCAGTTC

C.elegans B3:
(SEQ ID NO: 10)
CTGTGAACGGTCATCACC

C.elegans LoopF:
(SEQ ID NO: 11)
ACGGACATGTCGATCATGGA

C.elegans LoopB:
(SEQ ID NO: 12)
CGTCTCCCTTCAATCCGATGGC

BRCA1 FIP:
(SEQ ID NO: 13)
ATCCCCAGTCTGTGAAATTGGGCAAAATGCTGGGATTATAGATGT

BRCA1 BIP:
(SEQ ID NO: 14)
GCAGCAGAAAGATTATTAACTTGGGCAGTTGGTAAGTAAATGGAAGA

BRCA1 F3:
(SEQ ID NO: 15)
TCCTTGAACTTTGGTCTCC

BRCA1 B3:
(SEQ ID NO: 16)
CAGTTCATAAAGGAATTGATAGC

BRCA1 LoopF:
(SEQ ID NO: 17)
AGAACCAGAGGCCAGGCGAG

BRCA1 LoopB:
(SEQ ID NO: 18)
AGGCAGATAGGCTTAGACTCAA

CFTR FIP:
(SEQ ID NO: 19)
CCAAAGAGTAAAGTCCTTCTCTCTCGAGAGACTGTTGGCCCTTGAAGG

CFTR BIP:
(SEQ ID NO: 20)
GTGTTGATGTTATCCACCTTTTGTGGACTAGGAAAACAGATCAATAG

CFTR F3:
(SEQ ID NO: 21)
TAATCCTGGAACTCCGGTGC

CFTR B3:
(SEQ ID NO: 22)
TTTATGCCAATTAACATTTTGAC

CFTR LoopF:
(SEQ ID NO: 23)
ATCCACAGGGAGGAGCTCT

CFTR LoopB:
(SEQ ID NO: 24)
CTCCACCTATAAAATCGGC

Example 2

Detection of PCR Amplification Using a pH-Sensitive Visual Dye

The PCR reaction was performed in 50 mM KCl and 2.25 mM MgCl$_2$ using 500 nM each of the forward and reverse primers that amplify a 1.287 kb fragment from pAII17 plasmid DNA, 400 µM each of four dNTPs, 100 µM phenol red, 0.025 µl of 1M KOH, 1.875 U of Taq DNA polymerase in 25 µl. The PCR reaction was performed at 95° C. for 2 minutes, 36 cycles of 95° C. for 10 seconds, 62° C. for 15 seconds, 68° C. for 30 seconds. Before PCR cycling, all tubes, either with or without DNA template, had the same pink color. At the end of the PCR reaction, the triplicate reactions (labeled 1, 2 and 3; FIG. 5) that had DNA template changed color from pink to yellow while the reactions without DNA template (labeled 4, 5, and 6; FIG. 5) remained pink. DNA synthesis in the reactions containing template was confirmed using real-time PCR machine and agarose gel electrophoresis. Thus, the color change provided a reliable visual indicator for successful PCR reactions. Primer sequences were as follows:

1278bp_F:
(SEQ ID NO: 25)
AAAATCCAGCGCATGGGCGCGGCGTTCGCGGTTGAAGTCAAG
GG

1278bp_R:
(SEQ ID NO: 26)
CGCTTCGTGGATTACCAGCTTTTCTGGCGGTACTTCGTACTTG
C

Example 3

Visual Detection of Plasmid DNA in Bacterial Colonies

PCR reactions were performed in the presence of phenol red to identify E. coli colonies that were transformed to carry a specific plasmid DNA. A small portion of each colony was suspended in 10 µl water and 1 µl was added in the PCR reaction, which was performed as described in Example 2. Six colonies were tested with three colonies (1-3) from a plate that carries the same plasmid as used in the positive control (+) and three colonies (a-c) from a bacterial plate containing an unrelated plasmid. As in the positive control, the tubes that contained the target plasmid DNA changed color from pink to yellow (FIG. 6). The tubes that contained the unrelated plasmid remained pink just like the tube without any template (−). Thus, the color change in these PCR reactions allowed determination of colonies containing a specific plasmid DNA. This approach avoided a conventional step of using agarose gel electrophoresis to determine the PCR amplification, which is cumbersome and time consuming.

Example 4

Detection of SDA Amplification Using pH-Sensitive Visual Dyes

SDA reactions were performed in buffer-free reaction solution: 8 mM MgSO$_4$, 50 mM KCl, 10 mM (NH$_4$)$_2$SO$_4$, 0.4 mM dATP, 0.4 mM dGTP, 0.4 mM dTTP, 0.8 mM 2'-deoxycytidine-5'-O-(1-Thiotriphosphate) (dCTP-aS; TriLink BioTechnologies, San Diego, Calif.), 0.5 µM SDA primers, 0.2 U/µl BsoBI (New England Biolabs, Ipswich, Mass.), 0.32 U/µl Bst 2.0, pH 8.8. Final buffer concentration was 0.23 mM Tris from enzyme storage buffer carryover. Primer sequences were designed for human BRCA1 and contained the BsoBI restriction site. Reactions were incubated for 60 minutes at 65° C. in the presence of 100 µM pH-sensitive dye as indicated in FIG. 7A-B, with only reactions containing Bst 2.0 DNA polymerase changing color. This indicated successful detection of amplification based on pH decrease. Primer sequences were as follows:

```
SDAF:
                                                  (SEQ ID NO: 27)
ACCGCATCGAATGCATGTCTCGGGCAAAATGCTGGGATTATAGATGT

SDAR:
                                                  (SEQ ID NO: 28)
GGATTCCGCTCCAGACTTCTCGGGCAGTTGGTAAGTAAATGGAAGA

BF:
                                                  (SEQ ID NO: 29)
TCCTTGAACTTTGGTCTCC

BR:
                                                  (SEQ ID NO: 30)
CAGTTCATAAAGGAATTGATAGC
```

Example 5

Detection of LAMP Amplification Using pH-Sensitive Fluorescent Dyes

LAMP reactions were performed in buffer-free solution as in Example 1 using lambda (FIG. 8A-C) or CFTR (FIG. 9A-C) primers. The pH-sensitive fluorescent dyes BCECF-AM (2 μM) and SNARF-1 (10 μM) were used for reporting of amplification via decrease in pH. Fluorescence measurements were performed using a CFX-96 real time fluorimeter with dye spectra corresponding to: FAM channel, BCECF-AM; ROX channel, SNARF-1 high pH form; HEX channel, SNARF-1 low pH form. Drop in pH as measured by loss of fluorescence (BCECF-AM, SNARF-1 high pH form) or gain of fluorescence (SNARF-1 low pH form) was specific to the amplification reaction, as shown in FIG. 8A-C, where reactions lacking DNA polymerase exhibited no significant change in background. Time to fluorescence change was rapid (<10 minutes), indicating the efficiency and speed of the LAMP reaction. The detection was also quantitative, as shown in FIG. 9A-C, with clear distinction between serially diluted HeLa target DNA amounts.

Example 6

Detection of PCR Amplification Using a pH-Sensitive Fluorescent Dye

Three pairs of primers were used to amplify different sizes of amplicons. 309 bp and 1287 bp (from pAII17 plasmid DNA) and 114 bp (from *E. coli* genomic DNA) amplicons were used in PCR reactions performed as in Example 2 except 10 μM pH-sensitive fluorescent dye SNARF-1 was included in the reaction in place of the visual dye phenol red. The fluorescence reading was recorded in the ROX channel of the CFX96 machine. A significant drop of recorded signal was observed in the reactions containing DNA template during PCR cycling (FIG. 10A). Reactions that did not contain Taq DNA polymerase or DNA template (negative control) decreased slowly at a consistent rate due to pH change from thermal cycling. After subtracting the signal from the negative control, the reactions with template showed a dramatic signal decrease in FIG. 10B. The level of signal drop was proportional to the amplicon sizes. This example demonstrated that pH-sensitive fluorescent dyes can be used to monitor PCR reaction in real-time. In addition to 1287 bp primers listed above, primer sequences were as follows:

```
114bp_F:
                                                  (SEQ ID NO: 31)
AGCGGGGAGGAAGGGAGTAAAGTT

114bp_R:
                                                  (SEQ ID NO: 32)
CAGTATCAGATGCAGTTCCCAGGTT

309bp_F:
                                                  (SEQ ID NO: 33)
CTGGCCCACGAGGGCGAAGAGGCAGGCACCGGCCCGATCCT
GATG

309bp_R:
                                                  (SEQ ID NO: 34)
CGCCGCGCCCATGCGCTGGATTTTCGGTTCGGAGCCGTCACGGC
```

---

What is claimed is:

1. An aqueous preparation comprising: a non-naturally occurring pH-sensitive dye, a DNA polymerase, dNTPs in a formulation that contains a weak buffering agent in an amount of less than 1 mM Tris or equivalent or no buffering agent.

2. A preparation according to claim 1, further comprising primers.

3. A preparation according to claim 1, further comprising a template DNA.

4. A preparation according to claim 1, wherein the pH sensitive dye is either a visually detectable color dye or a fluorescent dye.

5. A method for detecting amplification of a nucleic acid; comprising:
   providing an amplification reaction mixture comprising the aqueous preparation of claim 1 and a template DNA; and
   detecting a change in spectral or fluorescent properties of the dye resulting from amplification of the target DNA.

6. The method according to claim 5, wherein the amplification method comprises an isothermal nucleic acid amplification or a polymerase chain reaction.

7. A method according claim 6, wherein the isothermal nucleic acid amplification method is selected from the group consisting of a loop-mediated isothermal amplification, a helicase displacement amplification, a strand displacement amplification, a recombinase polymerase amplification and a nicking enzyme amplification reaction.

8. A method according to claim 7, wherein the dye is soluble.

9. A method according to claim 8, wherein the soluble dye is a colored dye detectable in visible light.

10. A method according to claim 9, wherein the dye is selected from cresol red, phenol red, m-cresol purple, bromocresol purple, neutral red, naphtholphthalein, thymol blue, naphtolphthalein.

11. A method according to claim 8, wherein the dye is a fluorescent dye.

12. A method according to claim 11, wherein the fluorescent dye is a 2',7'-Bis-(2-Carboxyethyl)-5-(and-6)-Carboxyfluorescein or a carboxyl seminaphthorhodafluor.

13. A method according to claim 5, wherein the weakly buffered solution comprises less than 1 mM of Tris buffer or equivalent buffer.

14. A method according to claim 5, further comprising comparing a change in spectral or fluorescent properties of the pH sensitive dye from before to after the amplification reaction.

* * * * *